United States Patent [19]

Carter

[11] 3,972,956

[45] Aug. 3, 1976

[54] AVOIDING POLLUTION BY HF CATALYST RESIDUES IN ALKYLATION

[75] Inventor: Cecil O. Carter, Bartlesville, Okla.

[73] Assignee: Phillips Petroleum Company, Bartlesville, Okla.

[22] Filed: Apr. 11, 1975

[21] Appl. No.: 567,338

Related U.S. Application Data

[62] Division of Ser. No. 392,233, Aug. 28, 1973, Pat. No. 3,886,220.

[52] U.S. Cl. ........................................... 260/683.48
[51] Int. Cl.² ............................................ C07C 3/54
[58] Field of Search ................. 260/683.48, 683.49, 260/683.51, 683.42

[56] References Cited
UNITED STATES PATENTS

| | | | |
|---|---|---|---|
| 3,751,517 | 8/1973 | Hutson, Jr. et al. | 260/683.51 |
| 3,763,265 | 10/1973 | Hutson, Jr. et al. | 260/683.48 |
| 3,767,726 | 10/1973 | Hutson, Jr. et al. | 260/683.48 |
| 3,845,158 | 10/1974 | Sobel | 260/683.49 |
| 3,886,220 | 5/1975 | Carter | 260/683.48 |
| 3,911,044 | 10/1975 | Carter | 260/683.48 |

*Primary Examiner*—G. J. Crasanakis

[57] ABSTRACT

A used HF catalyst rerun unit comprises in tandem at least two strippers, a first to remove substantially all readily vaporizable components, e.g., light hydrocarbons and HF, and to separate acid-soluble oils as a liquid residue, and a second to produce rerun HF vapors and a stream of water containing HF. In an alkylation of a hydrocarbon operation, e.g., an isoparaffin by an olefin, said stream is used by reaction with an olefin to produce alkyl fluoride which can be fed to the alkylation reaction. Either before or after such reaction the stream is used to remove from noncondensible gas, as in a vent gas absorber, HF vapors therein contained and the stream returned to the HF rerun unit.

6 Claims, 1 Drawing Figure

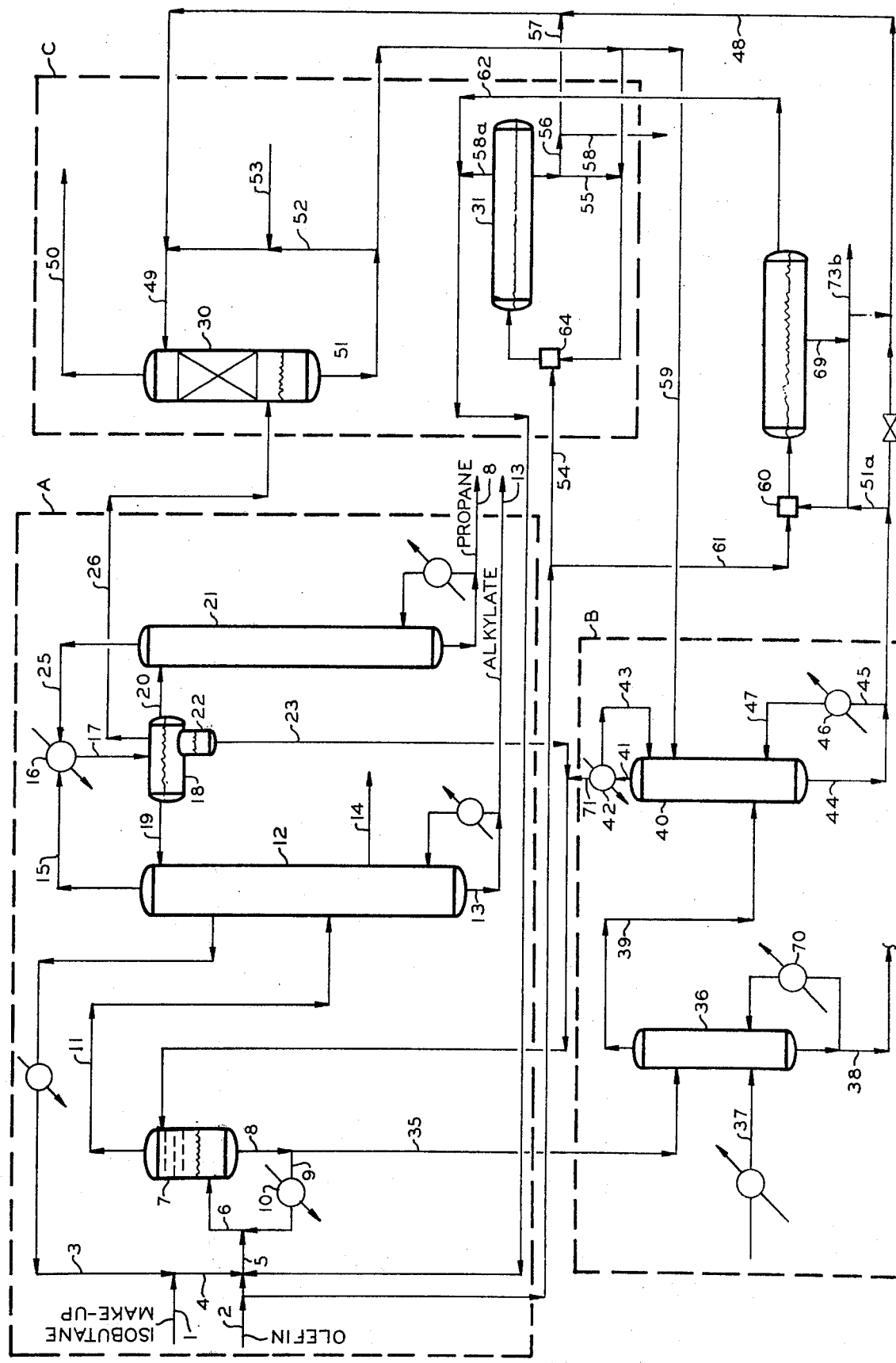

AVOIDING POLLUTION BY HF CATALYST RESIDUES IN ALKYLATION

This application is a division of my copending application having Ser. No. 392,233, filed Aug. 28, 1973, which issued as U.S. Pat. No. 3,886,220 on May 27, 1975 entitled "Avoiding Pollution by HF Catalyst Residues."

This invention relates to the recovery of HF normally unavoidably yielded from a process employing the same as a catalyst. It also relates to a method for the recovery of HF from noncondensibles normally yielded from a process employing HF as a catalyst. Further, the invention relates to an improved alkylation operation, e.g., alkylation of isoparaffin with an olefin wherein normally yielded HF is recovered from noncondensibles, converted, and returned for reuse in the process.

In one of its concepts, the invention provides a process for regenerating HF containing a hydrocarbon, acid-soluble oil, some water, and other impurities which comprises in a first zone separating by stripping with a hydrocarbon vapor all readily vaporizable HF thus to obtain an acid-soluble oil containing residue, treating overhead HF and hydrocarbon thus obtained under refluxing conditions to obtain a substantially purified HF and hydrocarbon stream and condensed water vapor containing HF. In another of its concepts, the invention provides a process as in the alkylation of hydrocarbons, for example, an isoparaffin with an olefin, e.g., isobutane and/or isopentane, with ethylene and/or higher molecular weight olefins such as propylene, a butylene, and amylene or a hexylene, wherein the alkylation is conducted in the presence of HF catalyst, as known in the art, wherein the HF catalyst is rerun as herein described and wherein the resulting water-HF stream obtained is caused to react with an olefin, e.g., as above named, to produce an alkyl fluoride phase which is passed to an alkylation reaction, for example, the original alkylation reaction or a subsequent one.

In a further concept, the water-HF from the stripping is used as described herein to absorb HF from noncondensible gases and returned to the stripping. Either before and/or after such use the water-HF from the stripping is contacted with olefin to form fluoride which is recovered and reused in the alkylation zone.

This invention will now be described with respect to an alkylation operation. It will be clear to one skilled in the art in possession of this disclosure, having studied the same, that the invention possesses applicability and adaptability to and in other operations in which HF catalyst is employed.

Pollution of the air with HF acid vapor and light hydrocarbons occurs when noncondensible gas is vented from, say, a depropanizer accumulator as known in the art. The venting is continuous. The vent gas heretofore has been neutralized in a closed system with, say, sodium or potassium hydroxide or otherwise chemically contacted with an agent of which a suitable disposition must be made. In any event, however the HF contaminating the vent gas has been recovered, there has been a disposal problem as in disposing of spent caustic combined with fluoride and a concomitant waste of the HF.

I have now conceived a process for recovering HF contained in such vent gases. I have also discovered a process for generating, in situ, in the alkylation operation, in which HF catalyst is rerun or regenerated, a reaction medium which can be used as absorbent for recovering from the vent gas the HF normally contained therein.

Thus, I have conceived that by operating the conventional HF-acid rerun operation in two stages, a first in which acid-soluble oil is removed by subjecting the used HF to stripping with a hydrocarbon, eg., hot isobutane, and a second in which the recovered HF and isobutane stream is refluxed to obtain a substantially purified HF-isobutane stream, I can obtain a water stream containing HF which can be used for a reaction with an olefin, e.g., as herein named, to generate an alkyl fluoride containing stream or phase which is then passed to the original alkylation or to a subsequent alkylation reaction or otherwise utilized in the process. Thus, the water containing HF is used as absorbent to scrub vent gas emanating from the process thus enriching still further the water with HF, which has now been removed from the vent gases which can, therefore, be vented safely, or can be used as a fluoride-free fuel gas following which this enriched water is reacted with an olefin to produce a stream containing alkyl fluoride which by its further utilization retains, in situ, in the system the HF.

It is an object of this invention to avoid atmospheric pollution in the venting of gases containing HF. It is another object of this invention to provide for the recovery from vent gases of HF contained therein. It is a further object of the invention to provide an improved alkylation operation wherein HF is used as a catalyst and there are obtained gases which are noncondensible and which normally, if vented, would cause pollution of the atmosphere. It is a further object of the invention to produce a fuel gas free from HF. A still further object of the invention is to economically operate an HF catalyzed reaction by reducing loss of HF therefrom.

Other aspects, concepts, objects, and the several advantages of the invention are apparent from a study of this disclosure, the drawing, and the appended claims.

According to the present invention, a used HF catalyst is stripped with a hot stripping vapor thus to obtain therefrom a heavy liquid residue, e.g., catalyst or acid-soluble oil, and a stream containing HF, stripping vapor and water vapor, said stream is then subjected to refluxing conditions to obtain therefrom substantially purified HF and stripping vapor and a condensed stream of water containing HF which then is caused to react with an olefin to produce an alkyl fluoride containing stream, which is recovered and utilized in the HF-catalyzed operation.

Also, according to the invention, the stream of water containing HF can be used directly to absorb HF vapors from vent gases and returned to said refluxing conditions and, as desired, either before or after said return contacted with an olefin to form alkyl fluoride, thus to produce a stream containing a lower HF.

Further according to the invention, there is provided a process for the alkylation of an alkylatable material with an alkylating agent employing HF as a catalyst wherein the water containing HF, the water having been introduced with the feedstocks, is obtained upon rerun of the used HF catalyst and the alkyl fluoride obtained, as described herein, is used either in the original or a subsequent alkylation step.

Given the foregoing description, one skilled in the art having studied the same can determine by mere routine testing the design and conditions of operation required to carry out the invention. However, to more fully describe the invention and to set forth the now best mode contemplated for it in its application to an alkylation operation, reference is had to the drawing.

For sake of convenience, three sections of the drawing have been framed and these are termed A, B, and C. Generally, A represents but for modifications owing to the invention being described herein a conventional isobutane-olefin alkylation in which are present a conventional isostripper and HF or propane recovery column. B represents an HF acid rerun unit according to the invention, and C represents a vent gas scrubbing operation which is operated in conjunction with A and B.

Isobutane and olefin are fed to the system by 1 and 2. Recycle isobutane from 3 is combined with the isobutane feed and passed through 4 together with olefin from 2 by 5 into riser-reactor 6 wherein it is intimately contacted with a stream of HF catalyst as known in the art. Catalyst is normally cycled from settler 7 by 8, 9, cooler 10, and 6 back to the settler. Reaction for the most part takes place in riser-reactor 6. In settler 7 there are formed a supernatant hydrocarbon phase passed by 11 to an isostripper 12 while the lower phase consisting of used HF acid is cycled as described.

The operation of isostripper 12 is conventional in this description in the sense that there are removed as bottoms by 13 an alkylate product containing stream, by 14 a normal butane containing stream, and overhead at 15 to cooler-condenser 16 a vaporous stream containing principally HF vapor, propane, and noncondensibles. Stream 15 now cooled as far as possible with ordinary cooling water available in the plant is passed by 17 to accumulator 18 from which a hydrocarbon phase formed is passed in part as reflux to the isostripper by 19 and in yield quantities by 20 to HF column 21. An acid phase 22 is recycled by passage by 23 into the upper portion of settler 7.

The isostripper and the HF column are reboiled as shown and as conventional in the art.

Bottoms stream 8 from the tower 21 constitute essentially propane substantially free from HF. Overhead 25 is passed from column 21 to the cooler-condenser 16 and thus recycled to accumulator 18. Gases, not condensed, pass by 26 into zone C.

In zone C there are provided a scrubber (or absorber) 30, a reactor 64, and a settler 31.

According to the present invention, as now described, scrubber 30 is supplied with a scrubbing or absorption medium from zone B. The scrubbing medium is enriched in HF in zone C and the enriched medium is used in reactor 64 to produce alkyl fluoride.

A portion of the acid passes from the foot of settler 7 by 35 to stripper 36. The stripper is heated and reboiled by hot isobutane vapors entering at 37 as well as by conventional reboiler 70. The used HF catalyst is stripped by countercurrent contact while it passes downwardly against the rising isobutane vapors in a manner and under conditions such that substantially only an acid-soluble oil residue is withdrawn at 38. HF, hydrocarbon vapor, and water vapor, according to the invention, pass overhead at 39 into a second stripper 40 which is refluxed with some of its own condensed overhead passed by 41 through condenser 42 and by 43 into a top portion of the column 40. Column 40 is reboiled by heating a portion of the bottoms stream, comprising water and HF withdrawn at 44 and passed by 45 to heater 46 and by 47 into the bottom of column 40.

Yield quantities of water and HF are taken by 48 into the top of scrubber 30 in section C. The point of entry of the water containing HF stream is selected to obtain the best or optimum desired scrubbing conditions so that gases vented from the system at 50 will be substantially free from HF. As shown, the absorbing medium entering at 49 is withdrawn at 51 and can by cycled by 52 to 49 and thence into the top portion of scrubber 30. There can be added directly to scrubber 30, as desired, additional scrubbing medium, for example, additional water; or additional water can be introduced at 53 into the cycling stream 52.

The bottoms 51 are passed to reactor 64 to which also is passed, in this embodiment, a portion of the olefin stream 2 fed to the process. Thus, olefin is fed by 54 into reactor 64 wherein a reaction between the olefin and HF in the water containing the same takes place. Phases are formed in settler 31 and a lower water phase removed at 55 is cycled to reactor 64 and/or by 56 and 57 to 48 and thence to the scrubber. Conditions are chosen in reactor 64 such as to substantially deplete the water phase of HF. To this end a series of countercurrently operated contactors can be employed in lieu of a single reactor as shown via 64. Liquid water accumulating in the system is removed at 58 and 73b from the process. This water will be only that water which together with the amount of water vapor emanating at 50 equals the water introduced into the system via the feedstocks. This relatively small quantity of water will now be treated as may be desired before it is discarded. Alkyl fluoride from 31 is passed to the alkylation reactor 6 by 58A, 62, and 5.

In Ser. No. 327,734, filed Jan. 29, 1973, by me there is described and claimed a process and apparatus for contacting a hydrogen fluoride containing vapors stream with a water stream to form a first mixture, reacting the first mixture with an olefin stream under conditions sufficient to form an alkyl fluoride and recovering an alkyl fluoride. The disclosure of this copending application is incorporated herein by reference.

In the application, conditions for the reaction in reactor 64 are given. The said conditions are now preferred.

Briefly, in reactor 64 there will be maintained a temperature in the range of from about 50° to about 150°F, preferably from about 90°F to about 110°F, at a pressure not substantially greater than about 300 pounds per square inch gauge. The olefin to HF weight ratio in the reactor will be from about 5 to 1 to about 5 to 2, and in any event such as to react out the HF from the HF-water extract or absorbent stream. Now preferred is a concentration of HF of 20–30 percent in the reaction mixture of HF, olefin, and water.

Depending upon the alkylation operation; in connection with which the drawing has been described as a specific example, the olefin in reactor 64 will be, preferably, isobutylene but can be and/or include any one of propylene, a normal butylene, an amylene, hexylene, etc. Specific examples of butylenes are butene-1, cis-butene-2, and trans-butene-2. Although the olefin can be added as a vapor or as a liquid or even contained in a suitable solvent or diluent, it is now preferably added as such in the liquid form.

While the absorber 30 conditions can be determined by mere routine testing by one skilled in the art in possession of this disclosure having studied the same, the conditions given in said copending application are now preferred and, briefly, are a temperature in the range of from about 50°F to about 150°F, preferably from about 90° to about 110°F, a pressure not substantially in excess of from about 300 psig, preferably about 150 to 200 psig, and the mol ratio of aqueous phase to mols of HF will be usually in the range of from about 3 to 1 to about 5 to 1. Usually the pressure will be optimum for good absorption and for feeding the gases to a fuel line system. It is desirable to maintain the concentration of HF in the HF-water extract or absorbent medium above about 15 weight percent, more preferably about 25 weight percent up to about 50 weight percent.

The specific conditions in area B of the drawing can be determined by one skilled in the art in possession of this disclosure having studied the same by routine calculations given the resulting streams he is to obtain.

Presently, the following conditions are now considered applicable and preferred. The pressure in stripper 36 will be approximately 25 pounds per square inch gauge albeit pressures in the range of from about 0 to about 50 pounds per square inch gauge can be employed. The stripping isobutane, at these pressures, will have a temperature of approximately 250°F, the kettle temperature of the stripper 36 will be approximately 315° to 320°F while the overhead will be approximately 200° to 260°F. The kettle temperature of stripper 40 will be approximately 200°–240°F while the overhead temperature will be approximately 160° to 200°F. Broader operating temperatures are applicable and in a given case such temperatures might be as much, more or less by 50°F or so. Importantly, depending upon the stripping medium, concentration of impurities, water present, and other factors which one skilled in the art of stripping fluids will taken into account the conditions given here will be found to be entirely satisfactory.

The following calculated example further illustrates the invention as applied in a specific instance, as discussed in connection with the drawing.

EXAMPLE

| | |
|---|---|
| Alkylate Production (unit size), BPD | 4,000 |
| Isobutane/Olefin Reactor Feed, volume ratio | 13.0 |
| Volume Alkylate Manufactured per volume olefin feedstock | 1.69 |
| Volume Isobutane Consumed/Unit volume olefin charge | 1.15 |
| Ethane Vented, bbls/1,000 bbls alkylate | 0.75 |
| HF Acid in rerun bottoms, lbs/bbl alkylate | 0.0546 |

TABLE I

Calculated Plant Material Balance in Barrels per Day

| Stream No.: | 1 | 2 | 3 | 8 | 13 | 14 | 15 | 35 | 37 | 38 | 48 | 50 |
|---|---|---|---|---|---|---|---|---|---|---|---|---|
| Stream Name: | Iso-butane Makeup | Ole-fin Feed | Re-cycle Iso-butane | Propane (Kettle Col. 21) | Alky-late | Normal Butane | Gaseous Ohd Col. 12 | Acid Chg. to Rerun Unit | Rerun Stripping Iso-butane | Acid-Soluble Oil Product | HF Water | Vent Gas Scrubber Residue |
| Constituents: | | | | | | | | | | | | |
| Ethane | | 3 | | | | | 3 | | | | | 3 |
| Propylene | | 962 | | | | | | | | | | |
| Propane | 7 | 307 | 4,042 | 458 | | | 16 | | | | | 16 |
| Isobutane | 2031 | 541 | 28,047 | 3 | 9 | 0.2 | | 75 | 150 | | | |
| n-Butane | 79 | 216 | 1,428 | | 289 | 5.7 | | | | | | |
| Butenes | | 1112 | | | | | | | | | | |
| Pentenes | | 293 | | | | | | | | | | |
| i & n & C$_{5+}$ | | 227 | 1,359 | | 4,227 | 0.1 | | | | | | |
| Isobutyl fluoride | | | | | | | | | | | | |
| HF | | | | | | | 0.2 | 420 | | | 0.6 | — |
| Water | | | | | | | | 4 | | Trace | 0.6 | |
| Acid-Soluble Oil | | | | | | | | 14 | | 13 | | |
| | 2117 | 3661 | 34,876 | 461 | 4,525 | 6.0 | 19.2 | 513 | 150 | 13 | 1.2 | 19 |
| Temperature | 90 | 90 | 110 | 118 | 100 | 100 | 115 | 90 | 250 | 315 | 230 | 90 |
| Pressure | 300 | 300 | 300 | 250 | 250 | 250 | 250 | 250 | 15 | 15 | 5 | 150 |

| Stream No.: | 51 | 52 | 54 | 54–61 | 55 | 57 | 58A | 62 | 69 | 71 |
|---|---|---|---|---|---|---|---|---|---|---|
| Stream Name: | Vent Gas Absorbent to Reactor 64 | Recycle Water to Vent Gas Absorber | Olefin to First Reactor 64 | Olefin to Second Reactor 60 | Recycle Water to Reactor 64 | Recycle Water from Settler | Alkyl Fluoride Return from First Reactor-Settler | Alkyl Fluoride Return from Second Reactor-Settler | Recycle Water to Second Reactor | Purified Acid Returned |
| Constituents: | | | | | | | | | | |
| Ethane | | | — | — | | | — | — | | |
| Propylene | | | 16 | 48 | | | 16 | 48 | | |
| Propane | | | 5 | 15 | | | 5 | 15 | | |
| Isobutane | | | 9 | 27 | | | 9 | 27 | | 225 |
| n-Butane | | | 4 | 12 | | | 4 | 12 | | |
| Butenes | | | 18.6 | 56 | | | 17.7 | 53.4 | | |
| Pentenes | | | 5 | 15 | | | 5 | 15 | | |
| i & n & C$_{5+}$ | | | 3.9 | 12 | | | 3.9 | 12 | | |
| Isobutyl fluoride | | | | | | | 1.1 | 3.2 | | |
| HF | 8.0 | 0.5 | — | — | 7.8 | 7.8 | — | — | 15.6 | 419.4 |
| Water | 24.0 | 1.5 | — | — | 23.4 | 23.4 | 0.4 | 1.1 | 46.4 | 3.4 |
| Acid-Soluble Oil | | | — | — | | | — | — | | 1 |
| | 32.0 | 2.0 | 61.5 | 185 | 31.2 | 31.2 | 62.1 | 186.7 | 62.0 | 645.8 |
| Temperature | 90 | 90 | 90 | 90 | 90 | 90 | 90 | 90 | 90 | 90 |
| Pressure | 350 | 175 | 350 | 350 | 325 | 325 | 325 | 325 | 325 | 5 |

The example shows that essentially 100 weight percent of the hydrogen fluoride normally lost in vent gas and acid rerun bottoms can be recovered using this invention. In considering the hydrogen fluoride consumption one should consider that combined fluorides will exist in the alkylate, propane, and normal butane. These losses plus any inefficiencies in vent gas and acid-soluble oil stripping, plus the probability of the feed being occasionally water-wet, will create conditions under which excess hydrogen fluoride water must be released from the unit requiring hydrogen fluoride make-up. The hydrogen fluoride recovery can be increased by operating at a 20 percent hydrogen fluoride content in the fluoride reactor rather than the now preferred 25 percent. Operation at a 20 percent hydrogen fluoride content will, however, require a higher olefin charge rate due to the lower conversion levels at this lower hydrogen fluoride content. The system is operable in a range of about 20 to 30 weight percent hydrogen fluoride in the reactor. At the upper limit, solubility of the fluorides in the water phase becomes excessive below 20 percent hydrogen fluoride and conversion in a single pass becomes quite low.

While the alkylation of isobutane has been described, the isoparaffin can also include or be isopentane or other low boiling isoparaffin.

While the specific embodiment herein shown as described the water-HF stream from the vessel 30 is admixed under fluoride forming conditions with olefin whereafter the HF depleted water, from which any unreacted olefin and fluoride have been removed, is discarded at 58, it is within the scope of the invention to return the water from the vent gas scrubber, enriched in HF to the stripper 40. It is also within the scope of the invention to a priori react the HF in the water-HF from the vessel 40 with olefin to form therein and to take therefrom fluoride prior to using said above-treated stream in vent gas absorber 30. Thus at 51a it is possible to remove the HF water used in the vent gas absorber from the system into reactor 60 there is fed at least a portion of the water-HF from 44 and therein the HF is reacted with olefin added from 54 by 61. One skilled in the art will, of course, operate the various portions of the process to achieve desired functions. For example, the water containing HF passing to absorber 30 must be of a concentration of HF of a quantity and of a temperature such that loss of HF from the absorber is substantially completely avoided. Now preferred is a concentration of HF such that when the water is used there will be no appreciable loss of HF with the vent gases and the bottoms 51 will contain less than about 50 percent HF in the water removed from 30.

Reasonable variation and modification are possible within the scope of the foregoing disclosure, the drawing, and the claims to the invention, the essence of which is that a hydrogen fluoride catalyst rerun operation is so conducted as to obtain in at least two stripping stages a rerun or purified stream containing HF and hydrocarbon and a water and HF stream which is suitable for absorbing from noncondensible gases HF vapor contained therein thus to recover the same within the operation in which generated following which the HF in the enriched absorbing medium is converted to alkyl fluorides by reacting an olefin therewith, the alkyl fluorides being suitable for use as in an alkylation reaction, alternatively, if not discarded the used water-HF stream is returned to the stripping without a priori reaction to form fluorides with the HF therein and then, in one modification of this variant, is now under fluoride forming conditions reacted with olefin, fluoride removed therefrom and then the thus-heated stream is used to absorb from noncondensible gases the HF-vapor contained therein.

I claim:

1. An alkylation process which comprises:
   a. reacting at least one isoparaffin with at least one olefin in the presence of an HF acid catalyst to produce an alkylation effluent,
   b. separating said effluent into an HF acid catalyst phase and a hydrocarbon phase,
   c. fractionating said hydrocarbon phase to recover alkylate and a vent gas stream comprising noncondensible gases lighter than propane including HF,
   d. passing said vent gas stream to a scrubbing zone,
   e. subjecting said HF acid catalyst phase to stripping with a hydrocarbon stripping medium under conditions to remove HF from said catalyst phase and to recover a stream comprising condensed water containing HF, and
   f. passing said condensed water containing HF from step (e) to said scrubbing zone and therein scrubbing said vent gas stream with said water containing HF to separate a vent gas stream free from HF and yielding an HF-enriched water-containing HF stream from said scrubbing zone.

2. A process according to claim 1 wherein said HF acid catalyst phase is treated in step (e) in two stages to recover the HF values in condensed water which comprises:
   1. contacting said HF acid catalyst phase in a first stage stripping zone with a hot hydrocarbon stripping medium under conditions sufficient to form an overhead stream comprising HF, water vapor, and hydrocarbon stripping vapor and a bottom stream comprising heavy liquid residue of acid-soluble oil and
   2. passing said overhead stream to a second stage stripping zone operated under refluxing conditions to produce an overhead stream comprising HF and hydrocarbon stripping medium and a bottom stream comprising condensed water containing HF.

3. A process according to claim 1 which comprises the additional steps of:
   g. passing a portion of said HF-enriched water-containing HF stream from said scrubbing zone to a first reaction zone and therein contacting said stream with an olefin under conditions to produce alkyl fluoride,
   h. passing the remainder of said HF-enriched water-containing HF stream from said scrubbing zone to said stripping zone to remove at least some of the HF therefrom, and
   i. contacting at least a portion of the bottoms stream comprising water containing HF removed from said stripping zone in a second reaction zone with an olefin under conditions which will produce an alkyl fluoride.

4. A process in accordance with claim 3 wherein the alkyl fluoride produced is recovered and introduced into the alkylation reaction of step (a).

5. A process according to claim 1 wherein at least a portion of said condensed water-containing HF stream obtained in step (e) is first admixed with an olefin under alkyl fluoride-forming conditions to produce alkyl fluoride therein, the alkyl fluoride is removed from said treated condensed water-containing HF stream, and then said treated stream is passed to said scrubbing zone in step (f).

6. A process according to claim 3 wherein the olefin in the alkyl fluoride-producing reaction is at least one selected from propylene, butene-1, cis-butene-2, trans-butene-2, isobutylene, an amylene, and a hexylene, the isoparaffin is selected from the group consisting of isobutane, isopentane or mixture thereof, the vent gases originate from a fractionation in which these gases are separated from propane and heavier hydrocarbons, and the alkyl fluoride-producing conditions include pressures up to about 300 psig, a temperature in the range of from 50° to about 150°F, and the olefin to HF weight ratio is in the range of about 5 to 1 to about 40 to 1.

* * * * *